(12) United States Patent
Ryu et al.

(10) Patent No.: US 10,664,968 B2
(45) Date of Patent: *May 26, 2020

(54) COMPUTER AIDED DIAGNOSIS APPARATUS AND METHOD BASED ON SIZE MODEL OF REGION OF INTEREST

(71) Applicant: Samsung Electronics Co., Ltd., Suwon-si, Gyeonggi-do (KR)

(72) Inventors: Seung Woo Ryu, Seoul (KR); Won Sik Kim, Gunpo-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 71 days.

This patent is subject to a terminal disclaimer.

(21) Appl. No.: 15/796,052

(22) Filed: Oct. 27, 2017

(65) Prior Publication Data
US 2018/0047164 A1 Feb. 15, 2018

Related U.S. Application Data

(63) Continuation of application No. 14/849,108, filed on Sep. 9, 2015, now Pat. No. 9,805,466.

(30) Foreign Application Priority Data

Sep. 16, 2014 (KR) .................. 10-2014-0122908

(51) Int. Cl.
*G06K 9/00* (2006.01)
*G06T 7/00* (2017.01)
(Continued)

(52) U.S. Cl.
CPC ............. *G06T 7/0012* (2013.01); *A61B 8/13* (2013.01); *A61B 8/56* (2013.01); *G06T 7/12* (2017.01);
(Continued)

(58) Field of Classification Search
None
See application file for complete search history.

(56) References Cited

U.S. PATENT DOCUMENTS 5,343,390 A * 8/1994 Doi ................. G06T 7/0012
382/132
5,734,742 A * 3/1998 Asaeda ................. G01N 21/88
382/107
(Continued)

FOREIGN PATENT DOCUMENTS

WO 2015/191414 A2 12/2015

OTHER PUBLICATIONS

Haas, Christine, et al. "Segmentation of 30 Intravascular Ultrasonic Images Based on a Random Field Model" Ultrasound in Medicine & Biology, vol. 26, No. 2 (2000): p. 297-306.
(Continued)

*Primary Examiner* — Shervin K Nakhjavan
(74) *Attorney, Agent, or Firm* — Jefferson IP Law, LLP

(57) ABSTRACT

A Computer Aided Diagnosis (CAD) apparatus and CAD method for detection of ROIs based on an ROI size transition model. The CAD apparatus includes: an image receiver configured to sequentially receive images; a region of interest (ROI) acquirer configured to acquire an ROI from a current image based on an ROI size transition model; and an ROI output configured to output visual information indicating the acquired ROI.

20 Claims, 13 Drawing Sheets

(51) Int. Cl.
  *A61B 8/00*     (2006.01)
  *A61B 8/13*     (2006.01)
  *G06T 7/12*     (2017.01)
  *G06T 7/143*    (2017.01)

(52) U.S. Cl.
  CPC .... *G06T 7/143* (2017.01); *G06T 2207/10016* (2013.01); *G06T 2207/10132* (2013.01); *G06T 2207/30096* (2013.01)

(56) References Cited

U.S. PATENT DOCUMENTS

| | | | | |
|---|---|---|---|---|
| 6,014,473 | A * | 1/2000 | Hossack | A61B 8/145 |
| | | | | 348/169 |
| 6,030,344 | A * | 2/2000 | Guracar | A61B 8/08 |
| | | | | 600/447 |
| 6,091,981 | A * | 7/2000 | Cundari | A61B 5/0053 |
| | | | | 600/407 |
| 6,368,277 | B1 * | 4/2002 | Mao | A61B 8/08 |
| | | | | 600/441 |
| 6,445,409 | B1 * | 9/2002 | Ito | G01S 3/783 |
| | | | | 348/155 |
| 7,263,472 | B2 | 8/2007 | Porikli | |
| 8,494,251 | B2 | 7/2013 | Camus | |
| 8,718,340 | B2 | 5/2014 | Madabhushi et al. | |
| 9,058,647 | B2 * | 6/2015 | Ishida | G06T 7/0012 |
| 9,123,096 | B2 * | 9/2015 | Miyasa | G06T 7/0012 |
| 9,504,436 | B2 * | 11/2016 | Suri | A61B 6/502 |
| 2002/0076108 | A1 * | 6/2002 | Konoshima | G06T 7/246 |
| | | | | 382/217 |
| 2003/0223631 | A1 * | 12/2003 | Ine | G06K 9/00 |
| | | | | 382/145 |
| 2003/0235327 | A1 * | 12/2003 | Srinivasa | G06K 9/3241 |
| | | | | 382/104 |
| 2004/0143189 | A1 | 7/2004 | Lysyansky et al. | |
| 2005/0069208 | A1 * | 3/2005 | Morisada | G06K 9/00228 |
| | | | | 382/190 |
| 2005/0171409 | A1 * | 8/2005 | Arimura | G06T 7/0012 |
| | | | | 600/300 |
| 2005/0248676 | A1 | 11/2005 | Christenson | |
| 2005/0259854 | A1 * | 11/2005 | Arimura | G06T 7/0012 |
| | | | | 382/130 |
| 2006/0222221 | A1 * | 10/2006 | Sathyanarayana | G06K 9/6292 |
| | | | | 382/128 |
| 2008/0002857 | A1 * | 1/2008 | Tsunashima | H04N 7/18 |
| | | | | 382/103 |
| 2008/0111883 | A1 * | 5/2008 | Maolin | G08B 13/19602 |
| | | | | 348/143 |
| 2008/0253631 | A1 * | 10/2008 | Oosawa | G16H 15/00 |
| | | | | 382/128 |
| 2008/0317314 | A1 * | 12/2008 | Schwartz | G06K 9/34 |
| | | | | 382/131 |
| 2009/0003652 | A1 * | 1/2009 | Steinberg | G06K 9/00228 |
| | | | | 382/103 |
| 2009/0136126 | A1 | 5/2009 | Tsurata | |
| 2009/0213263 | A1 * | 8/2009 | Watanabe | H04N 5/23212 |
| | | | | 348/349 |
| 2009/0300692 | A1 | 12/2009 | Mavlankar et al. | |
| 2009/0303342 | A1 * | 12/2009 | Corcoran | G06K 9/00228 |
| | | | | 348/222.1 |
| 2010/0054538 | A1 * | 3/2010 | Boon | G06K 9/00798 |
| | | | | 382/104 |
| 2010/0104505 | A1 * | 4/2010 | O'Connor | A61B 6/0414 |
| | | | | 424/1.11 |
| 2011/0081068 | A1 | 4/2011 | Brinks et al. | |
| 2011/0152687 | A1 | 6/2011 | Iimura et al. | |
| 2011/0249961 | A1 * | 10/2011 | Brunner | H04N 5/23216 |
| | | | | 396/213 |
| 2012/0020519 | A1 * | 1/2012 | Yashiro | G06K 9/00369 |
| | | | | 382/103 |
| 2012/0062717 | A1 * | 3/2012 | Kinouchi | A61B 1/00009 |
| | | | | 348/74 |
| 2013/0027511 | A1 * | 1/2013 | Takemura | G06K 9/00798 |
| | | | | 348/42 |
| 2013/0058575 | A1 * | 3/2013 | Koo | G06K 9/3258 |
| | | | | 382/176 |
| 2013/0103299 | A1 * | 4/2013 | Matsuda | G06F 17/00 |
| | | | | 701/300 |
| 2013/0170724 | A1 * | 7/2013 | Kim | G06T 15/00 |
| | | | | 382/131 |
| 2013/0195339 | A1 * | 8/2013 | Endo | G06K 9/46 |
| | | | | 382/131 |
| 2013/0338493 | A1 | 12/2013 | Durvasula et al. | |
| 2014/0085324 | A1 | 3/2014 | Charvet et al. | |
| 2014/0235267 | A1 * | 8/2014 | Song | G05D 1/0253 |
| | | | | 455/456.1 |
| 2014/0330107 | A1 * | 11/2014 | Shin | G06T 7/0016 |
| | | | | 600/411 |
| 2015/0238158 | A1 * | 8/2015 | Zhou | G06T 7/0012 |
| | | | | 382/131 |
| 2015/0320320 | A1 | 11/2015 | Kopelman et al. | |
| 2018/0092537 | A1 * | 4/2018 | Endo | G06T 11/00 |

OTHER PUBLICATIONS

Katouzian, Amin, et al. "A State-of-the-Art Review on Segmentation Algorithms in Intravascular Ultrasound (IVUS) Images." Information Technology in Biomedicine, IEEE Transactions, vol. 16, No. 5 (Sep. 2012): 823-834.

Extended European Search Report dated Mar. 2, 2016 in counterpart European Application No. 15185456.9. (8 pages in English).

European Office Action dated Jun. 14, 2018, issued in the European Application No. 15185456.9.

* cited by examiner

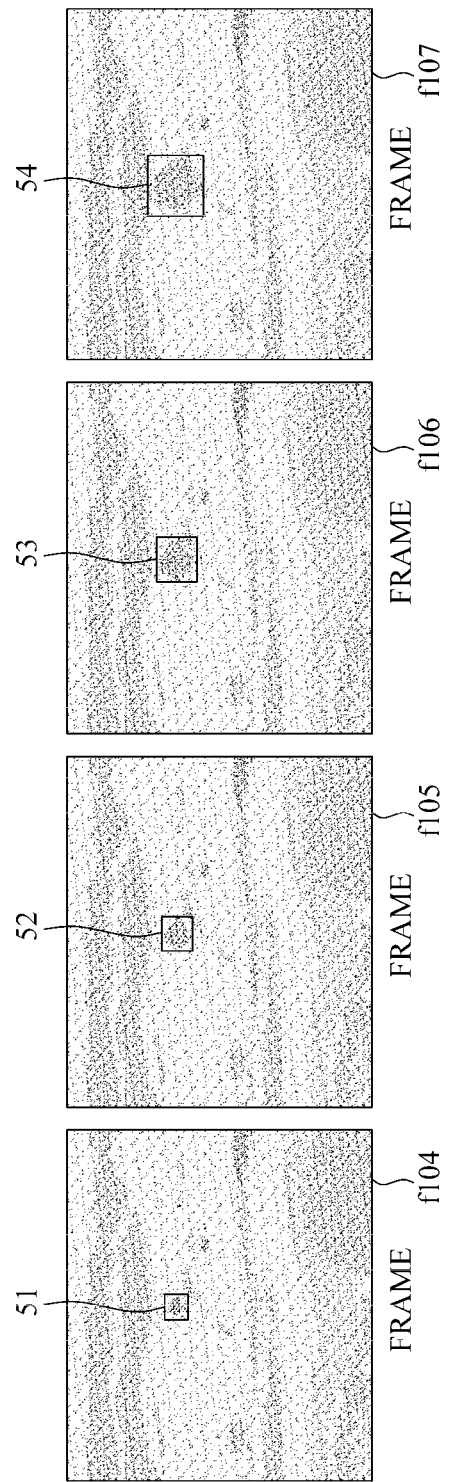

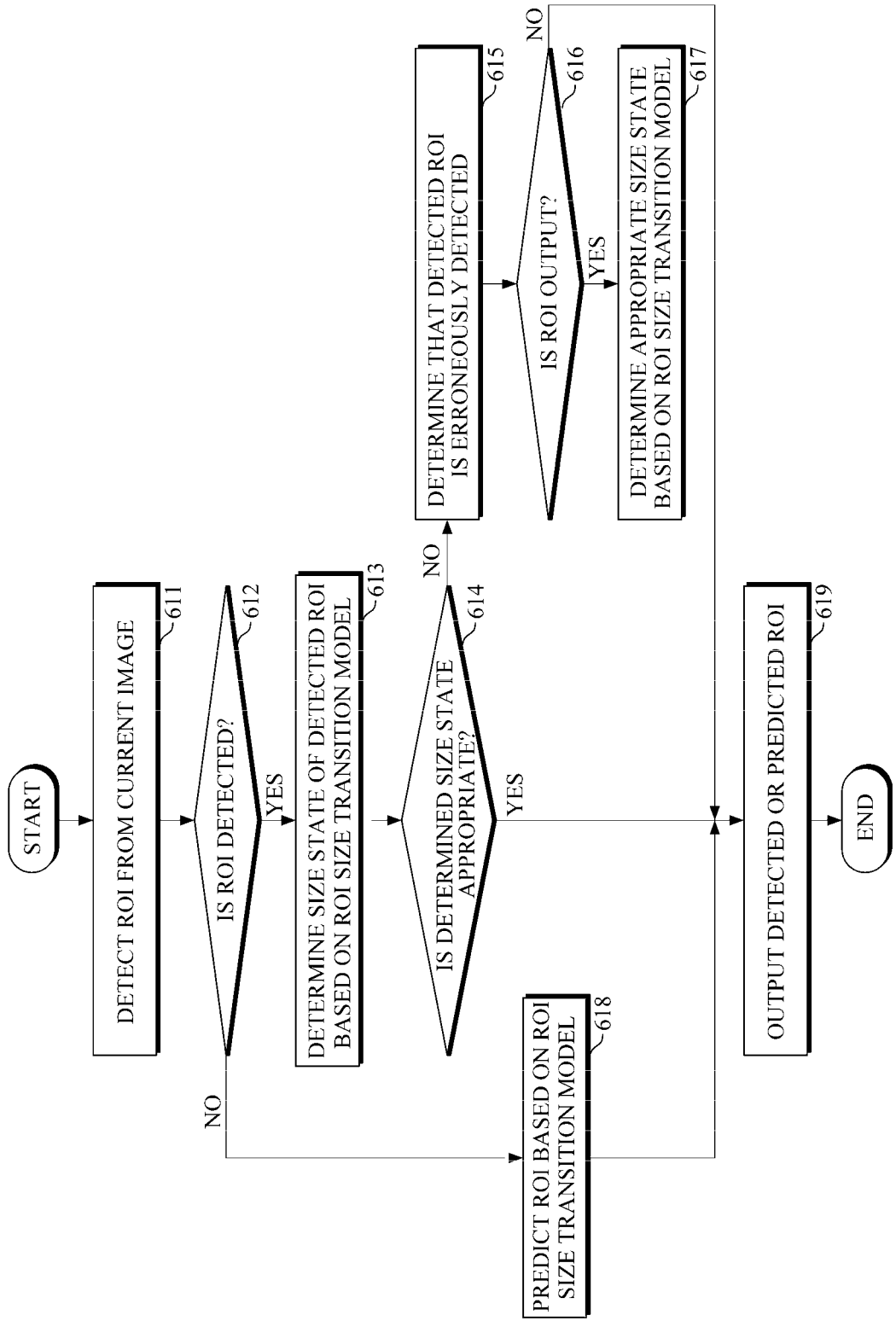

COMPUTER AIDED DIAGNOSIS APPARATUS AND METHOD BASED ON SIZE MODEL OF REGION OF INTEREST

CROSS-REFERENCE TO RELATED APPLICATION(S)

This application is a continuation application of prior application Ser. No. 14/849,108, filed on Sep. 9, 2015, which will issue as U.S. Pat. No. 9,805,466 on Oct. 31, 2017 and claimed the benefit under 35 U.S.C § 119(a) of a Korean Patent filed on Sep. 16, 2014 in the Korean Intellectual Property Office and assigned Serial number 10-2014-0122908, the entire disclosure each of which are hereby incorporated by reference.

BACKGROUND

1. Field

The following description relates to a Computer Aided Diagnosis (CAD) apparatus and method for supporting detection and display of a region of interest based on a region of interest (ROI) size transition model.

2. Description of Related Art

In the medical diagnosis field, ultrasound images are used to diagnose patients' conditions. Medical practitioners generally apply a probe to a patient's body parts to acquire ultrasound images in real time, check the acquired ultrasound images output to a screen with the naked eye, detect and determine a lesion or a suspected region. If there is a region suspected to include a lesion, medical practitioners move the probe slowly or stop the probe to observe the suspected region.

The computer aided diagnosis (CAD) system analyzes various medical images to detect lesions, and determines whether detected lesions are benign or malignant to provide the diagnosis results to medical practitioners. In a general CAD system, ultrasound imaging diagnosis is performed such that a lesion is first identified using ultrasound, and then is determined by a separate CAD system. Research on the real-time CAD system is currently being conducted where a lesion is detected from ultrasound images acquired in real time to diagnose the lesion.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a Computer Aided Diagnosis (CAD) apparatus, including an image receiver configured to sequentially receive images, a region of interest (ROI) acquirer configured to acquire an ROI from a current image based on an ROI size transition model, and an ROI output configured to output visual information indicating the acquired ROI.

The image receiver may receive in real time ultrasound images acquired through a probe in units of frames.

The ROI acquirer may include an ROI detector configured to detect one or more ROIs from the current image.

The ROI acquirer may further include an ROI determiner configured to determine whether a ROI from the one or more detected ROIs is erroneously detected based on the ROI size transition model.

The determiner may be configured to determine a size state of the detected ROI by matching the size of the detected ROI with the ROI size transition model, and determine that the detected ROI is erroneously detected, in response to determining that a size state of a previous image on the ROI size transition model is not capable of being transformed to the determined size state of the current image.

In response to the detected ROI being erroneously detected, the ROI output component may be further configured to not output visual information on the detected ROI.

In response to the detected ROI being erroneously detected, the ROI output component may be further configured to determine the biggest size state that is possible to transition from the size state of the previous image using the ROI size transition model, and to output visual information on the detected ROI that has a size corresponding to the biggest size state.

The ROI acquirer may further include an ROI predictor configured to predict an ROI in the current image using the ROI size transition model, in response to the ROI not being detected from the current image.

The ROI predictor may determine a size state transitionable from the size state of the ROI acquired from the image before the current image using the ROI size transition model, and to predict the ROI in the current image using the determined size state.

The ROI size transition model may be created using the Markov model learning based on a change in sizes of ROIs in a sequence of images for each interested item, and the ROI size transition model comprises size states, a transition possibility between the size states, transition direction, and transition probability information.

In order to indicate a location and size of the ROI in the current image that is output on the screen, the visual information may include first information comprising at least one of square, round, oval, or cross shapes, and second information comprising at least one of color, types of lines, or thickness of lines of the first information.

The visual information may be output on a screen.

The ROI acquirer may be configured to detect the one or more ROIs based on geo-spatial location information of the one or more ROIs.

In another general aspect, there is provided a Computer Aided Diagnosis (CAD) method, including: sequentially receiving images; acquiring a region of interest (ROI), at a processor, from a current image based on an ROI size transition model, and outputting visual information that indicates the acquired ROI.

The acquiring of the ROI may include detecting one or more ROI from the current image.

The acquiring of the ROI may include, determining whether a ROI from the one or more detected ROI is erroneously detected based on the ROI size transition model.

The determining of the ROI may include determining a size state of the detected ROI by matching the size of the detected ROI with the ROI size transition model, and determining that the detected ROI is erroneously detected, in response to determining that a size state of a previous image on the ROI size transition model is not capable of being transformed to the determined size state of the current image.

The outputting of the ROI may include, in response to the detected ROI being erroneously detected, the outputting of the ROI comprises not outputting visual information on the detected ROI.

In response to the detected ROI being erroneously detected, the outputting of the ROI may include determining the biggest size state that is possible to transition from the size state of the previous image using the ROI size transition model, and outputting visual information on the detected ROI that has a size corresponding to the biggest size state.

The acquiring of the ROI may include predicting an ROI in the current image using the ROI size transition model in response to the ROI not being detected from the current image.

The predicting of the ROI may include determining a size state transitionable from the size state of the ROI acquired from the image before the current image using the ROI size transition model, and predicting the ROI in the current image using the determined size state.

The ROI size transition model may be created using the Markov model learning based on a change in sizes of ROIs in a sequence of images for each interested item, and the ROI size transition model may include size states, a transition possibility between the size states, transition direction and transition probability information.

In another general aspect, there is provided a Computer Aided Diagnosis (CAD) apparatus, including an image receiver configured to sequentially receive images, a region of interest (ROI) acquirer configured to acquire one or more ROIs from a current image based on an ROI size transition model, and a model builder configured to extract model information from the received images and the one or more ROIs.

The model information may include at least one of a size of a ROI visual information from the one or more detected ROIs, the shape of the ROI visual information, the geo-spatial location of the ROI visual information, or a number of pixels.

Other features and aspects will be apparent from the following detailed description, the drawings, and the claims.

BRIEF DESCRIPTION OF THE DRAWINGS

FIGS. 5A to 5C are diagrams illustrating examples of an ROI size transition model.

FIG. 9 is a diagram illustrating an example of acquiring of an ROI.

Figure 1:
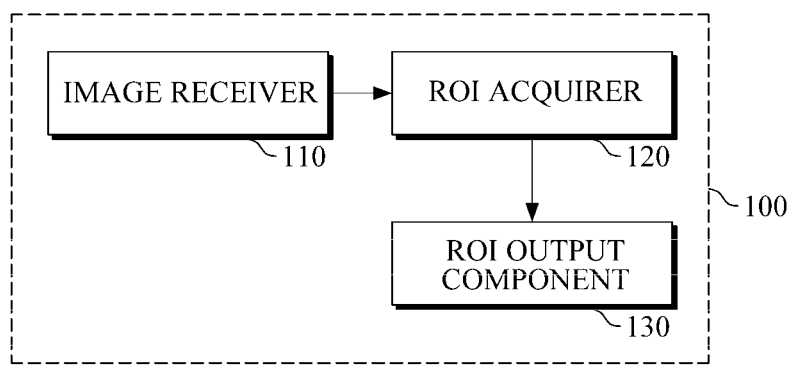
FIG. 1 is a diagram illustrating an example of a Computer-Aided Diagnosis (CAD) apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses, and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 is a diagram illustrating an example of a Computer-Aided Diagnosis (CAD) apparatus.

The CAD apparatus 100 analyzes ultrasound images acquired in real time through a probe to detect and classify regions of interest (ROIs). However, the CAD apparatus 100 is not limited thereto, and may include an apparatus that receives a sequence of images acquired in real time or a sequence of pre-acquired images using various image capturing devices to detect and classify ROIs. Referring to FIG. 1, the CAD apparatus 100 includes an image receiver 110, an ROI acquirer 120, and an ROI output component 130.

The image receiver 110 sequentially receives images, where the images may be successively captured medical images of examined regions of a subject. For example, a user that performs examination applies a probe to a diseased area, such as, for example, lesion, fingers, toes, abdomen, breast, and chest of a subject and moves the probe around the area to acquire images. The image receiver 110 may receive the images in real time. Images may be transmitted in units of frames in real time, and the image receiver 110 transmits the images received in real time to the ROI detector 120 for processing. The ROI detector 120 may acquire an ROI from a current image every time an image is received. The ROI refers to a region that includes items of interest for the purposes of diagnosis, such as, for example, lesion, fingers, toes, abdomen, breast, and chest. The ROI detector 120 may acquire an ROI from a current image based on an ROI size transition model. The ROI size transition model may be created in advance based on a change in sizes of ROIs in a sequence of images for each ROI. The above-described creation of the ROI size transition model is a non-exhaustive example, and other methods of creating the ROI size transition model are considered to be well within the scope of the present disclosure. For example, the size model may be created by a user without learning. In another example, the ROI size transition model may be created by learning, or may be a Markov model that is created in the form of rules. The ROI size transition model may include size states, transition possibility between the size states, a transition direction, and transition probability information, which will be described in further detail with reference to FIG. 4.

In one example, the ROI acquirer 120 may acquire an ROI using an automatic detection algorithm. Upon detecting an ROI, an ROI size transition model may be used to determine whether the ROI is erroneously detected.

In another example, where an ROI is not detected from a current image using an automatic detection algorithm, an ROI may be predicted in the current image based on information on an ROI tracked in a previous image and an ROI size transition model.

The ROI output component 130 outputs an ROI detected by the ROI acquirer 120 to be displayed on a screen. Based on the location and size of the detected ROI, the ROI output component 130 may output an ROI for display on a screen by outputting visual information associated with the ROI at a position that corresponds to a current image output to a screen. In order to display the size and location of an ROI, the visual information may include first information regarding shapes, such as, for example, square, round, oval, and cross. The visual information may also include information regarding color, types and thickness of lines, and the like.

In one example, if the ROI acquirer 120 determines that an automatically detected ROI is erroneously detected, the ROI output component 130 may not output visual information on the ROI.

In another example, if an ROI detected from a current image is an ROI that has been tracked from a previous image, and the ROI is determined to be detected erroneously, the ROI output component 140 may determine the size state of the ROI appropriate for a current image using an ROI size transition model, and may output on a screen visual information having a size corresponding to the determined size state. In this case, a maximum possible size state that may be transitioned from the size state of an ROI detected from a previous image may be determined to be a size state appropriate for a current image.

It may be predetermined by a user whether to output an ROI that is erroneously detected from a current image. For example, in such a case visual information may not be output for an ROI that is newly detected from a current image, and visual information may be output for an ROI that has been tracked from a previous image.

Figure 2:
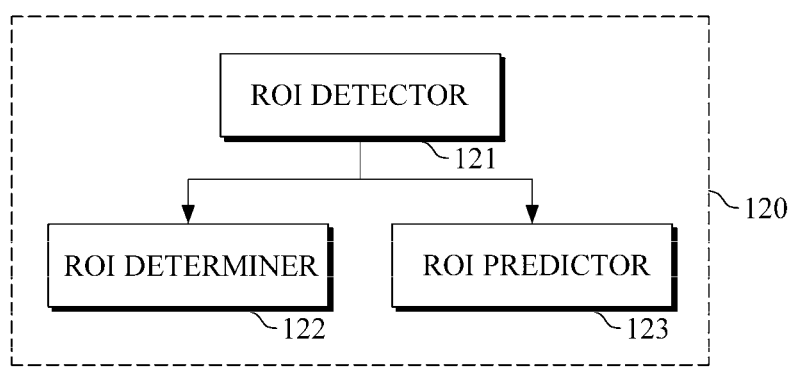
FIG. 2 is a diagram illustrating an example of the ROI acquirer of FIG. 1.

FIG. 2 is a diagram illustrating an example of a ROI acquirer of FIG. 1. Referring to FIG. 2, the ROI acquirer 120 includes an ROI detector 121, an ROI determiner 122, and an ROI predictor 123.

The ROI detector 121 may detect an interested item by applying an detection algorithm of an ROI to a received current image, and may determine a region that includes the interested item to be an ROI. Examples of the ROI detection algorithm may include algorithms such as, for example, AdaBoost, Deformable Part Models (DPM), Deep Neural Network (DNN), Convolutional Neural Network (CNN), Sparse Coding. The algorithm(s) to be applied may be determined depending on factors such as, for example, the performance of the apparatus 100, diagnosis purposes, and diagnosis time.

Once an ROI is detected from a current image, the ROI determiner 122 may track the ROI, and determine whether the ROI is identical to an ROI that has been detected from a previous image. In one example, using geo-spatial location information of the detected ROI, the location of the ROI is compared to a location of an ROI detected from a previous image to determine whether the two regions of interest are identical. In another example, it may be determined whether the detected ROI and an ROI that has been tracked are identical to each other using techniques such as, for example, Jaccard similarity algorithm, and Mean shift algorithm.

Figure 3:
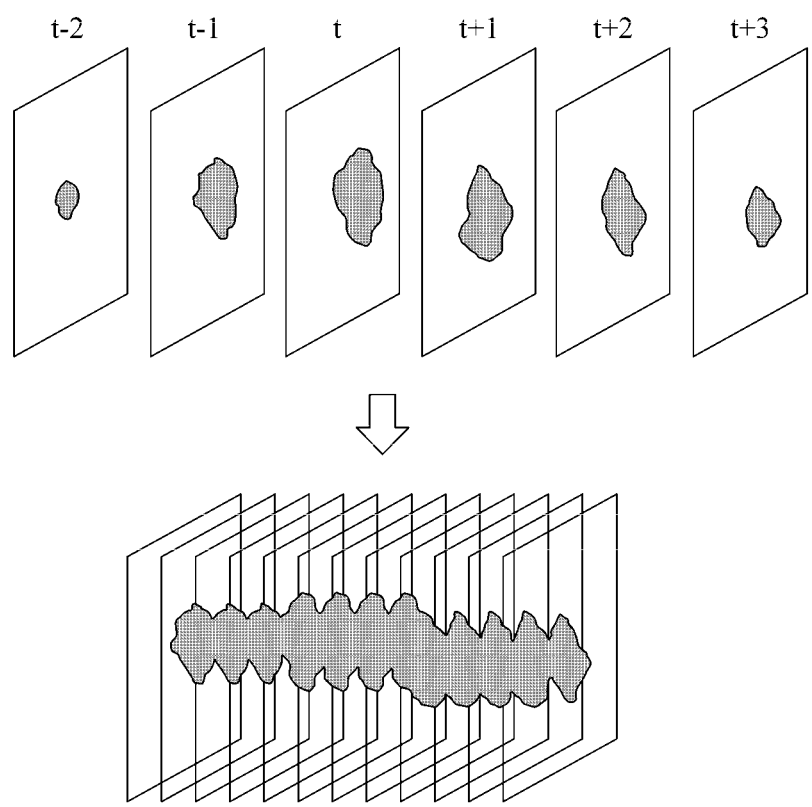
FIG. 3 is a diagram illustrating an example of an ROI in a sequence of images.

FIG. 3 is a diagram illustrating an example of an ROI in a sequence of images. As illustrated in FIG. 3, an item of interest, such as a lesion, is generally three-dimensional. The size of an three-dimensional ROI is gradually increases from a point in time (t−2) when the ROI is initially detected to a point in time (t+3) when the ROI is lastly detected, and then the size decreases. Referring to FIG. 3, the ROI is small at (t−2) when it is initially detected, and then is gradually increased to a maximum size at a current time (t). The size of the detected ROI gradually decreased after the points in time t+1 to t+3.

As illustrated in FIG. 3, once an ROI is detected from a current image, the ROI determiner 122 may determine whether the detected ROI is erroneously detected based on a change in size of an ROI.

For example, assuming that no ROI is detected from an image at a previous time t−1, if an ROI having a size as illustrated in FIG. 3 is detected for the first time from an image of a current time (t), the ROI determiner 122 may determine that the ROI is erroneously detected. Where an ROI, as illustrated in FIG. 3, is detected for the first time, an ROI having a size corresponding to the size of an ROI detected at a point in time t−2 is normally detected, with no possibility of suddenly detecting an ROI having a size bigger than the size, such that it is determined that the ROI is erroneously detected. In another example, while an ROI has been tracked in previous images during points in time (t−2, . . . , and t−1), if an ROI having a size that is not normal in an image of a current time (t), e.g. a size that is not possible to be detected immediately after a size of an ROI detected from a previous image at t−1, the detected ROI may be determined to be erroneously detected.

The ROI determiner 122 may determine the size state of a detected ROI by matching the size of an ROI detected from a current image with an ROI size transition model. Once the size state is determined, it is determined whether it is possible to transition from the size state of an ROI detected from a previous image, and based on the determination, it may be determined whether an ROI is erroneously detected.

If an ROI is not automatically detected from a current image, the ROI predictor 123 may predict an ROI that is appropriate for a current image using an ROI size transition model. In general, an ROI, which has been tracked from a previous image, does not suddenly disappear at a certain point. Where an ROI, which has been tracked from a previous image, disappears suddenly from a current image, the ROI predictor 123 may determine that an ROI, which is to be detected, is not detected, and may predict an ROI having a size appropriate to be detected from a current image.

For example, the ROI predictor 123 may identify a change in size using ROI tracking information in previous images, i.e., using information on the size of an ROI acquired from a previous image, and may determine a size state that is likely to be detected from a current image on an ROI size transition model. Further, using ROI location information of a previous image, the ROI predictor 123 may determine the location of an ROI in a current image.

Figure 4:
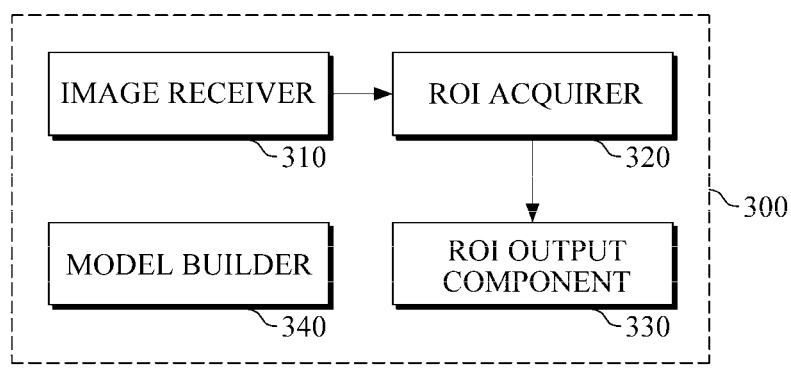
FIG. 4 is a diagram illustrating an example of a Computer-Aided Diagnosis (CAD) apparatus.

FIG. 4 is a diagram illustrating an example of a Computer-Aided Diagnosis (CAD) apparatus according to another example. Referring to FIG. 4, the Computer Aided Diagnosis (CAD) apparatus 300 includes an image receiver 310, an ROI acquirer 320, an ROI output component 330, and a model builder 340. The above descriptions of FIGS. 1-3 is also applicable to the image receiver 310, the ROI acquirer 320, and the ROI output component 330 shown in FIG. 4, and is incorporated herein by reference. Thus, the above description may not be repeated here.

The model builder 340 may build an ROI size transition model based on the change in size of an ROI desired by a user in a sequence of collected images.

The model builder 340 may collect a sequence of 3D video data successively captured to acquire an ROI, or video data acquired in real time, and may extract ground truth from the collected data to build an ROI size transition model. The ground truth may include information, such as, for example, the size of an ROI visual information, the shape of an ROI visual information (such as, for example, a square shape, an oval shape, a round shape, a cross mark), and a number of pixels.

The model builder 340 may generate an ROI size transition model by a methodology such as, for example, the Markov Model learning based on the extracted ground truth. Further, in the case where a user is well aware of the change in size of an ROI through specialized knowledge, diagnosis experiences, or the like, an ROI size transition model may be directly generated by the user without specific learning.

Figure 5A:
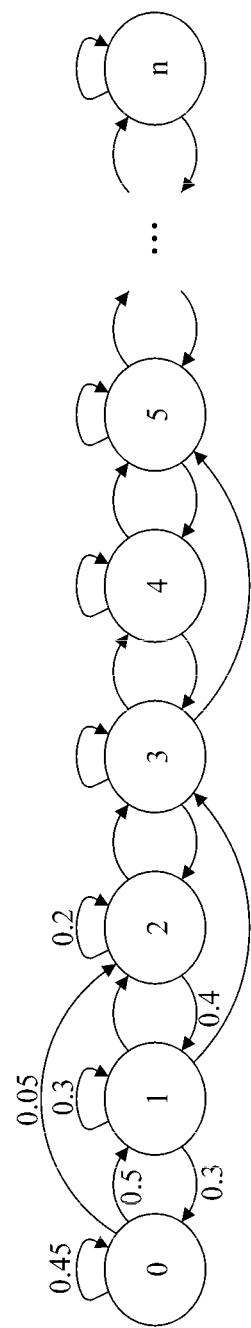
Figure 5C:
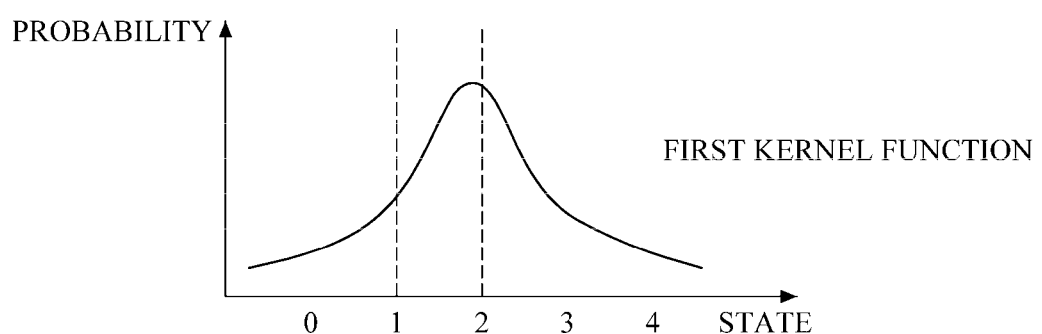

FIGS. 5A to 5C are diagrams explaining an ROI size transition model according to an example. Referring to FIGS. 4, 5A, and 5B, the model builder 340 may generate a size transition model that includes information such as, for example, size states (0, 1, 2, . . . , n−1, and n), probability of transition between the size states (0, 1, 2, . . . , n−1, and n), and transition probability information as illustrated in FIG. 5A, in which size state 0 denotes a state where an ROI is not detected, size state 1 denotes the smallest size of an ROI, and size state n denotes the largest size of an ROI.

As illustrated in FIG. 5B, assuming that four successive image frames f104, f105, f106, and f107 include ROIs 51, 52, 53, and 54, respectively, and the sizes of the ROIs increase in order from 51 to 54. The model builder 340 may define, as states 1, 2, 3, and 4, the sizes of the ROIs 51, 52, 53, and 54 detected from each of the four successive image frames f104, f105, f106, and f107.

The model builder 340 may calculate probability of transition between each state using Equation 1, and the calculated probability of transition between each state is illustrated in FIG. 5C. For example, if a current n−1 frame has state 1 (e.g., 10 mm² in size), and the size of an ROI detected from the n frame is 12 mm², the transition from state 1 to state 2 may be calculated to have the highest probability as illustrated in FIG. 5C.

$$P(B_{n,m}|B_{n-1,m},B_{n-2,m}) \propto P(S_{n,m}|S_{n-1,m},S_{n-2,m}) \cdot f(D_{B_m})$$ Equation 1

Here, B represents the size of a detected ROI, S represents a size state of the ROI, D represents a detection score of the ROI, n denotes frame n, and m denotes an index of the ROI interest detected from frame n. For example, $B_{n,m}$ denotes an $m^{th}$ ROI detected from frame n.

Figure 6A:
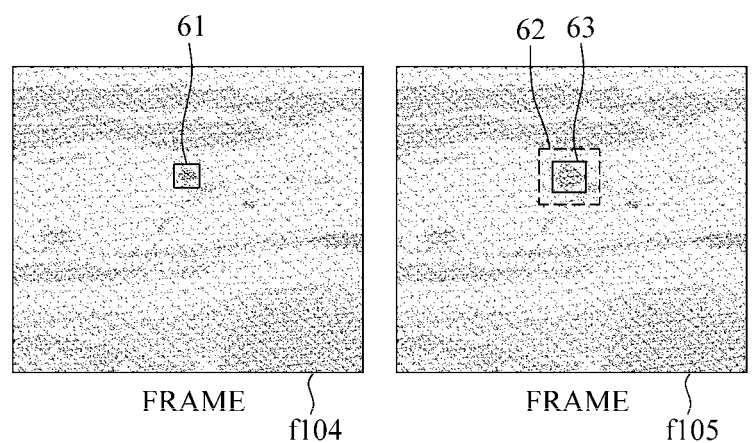
FIGS. 6A and 6B are diagrams illustrating examples of acquiring and outputting of an ROI.
Figure 6B:
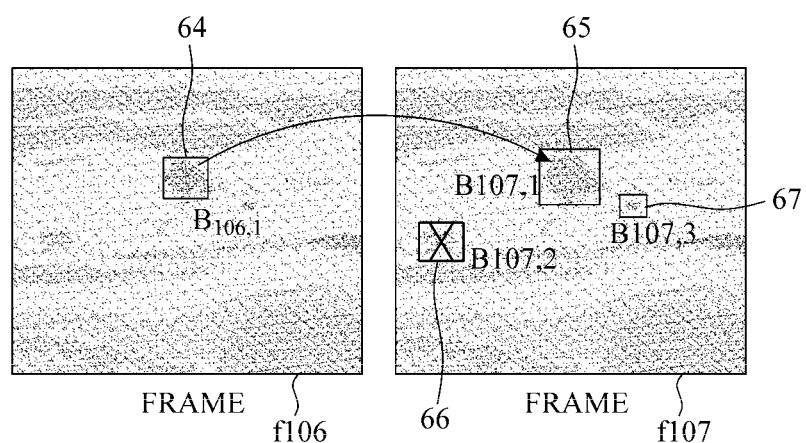
Figure 7A:
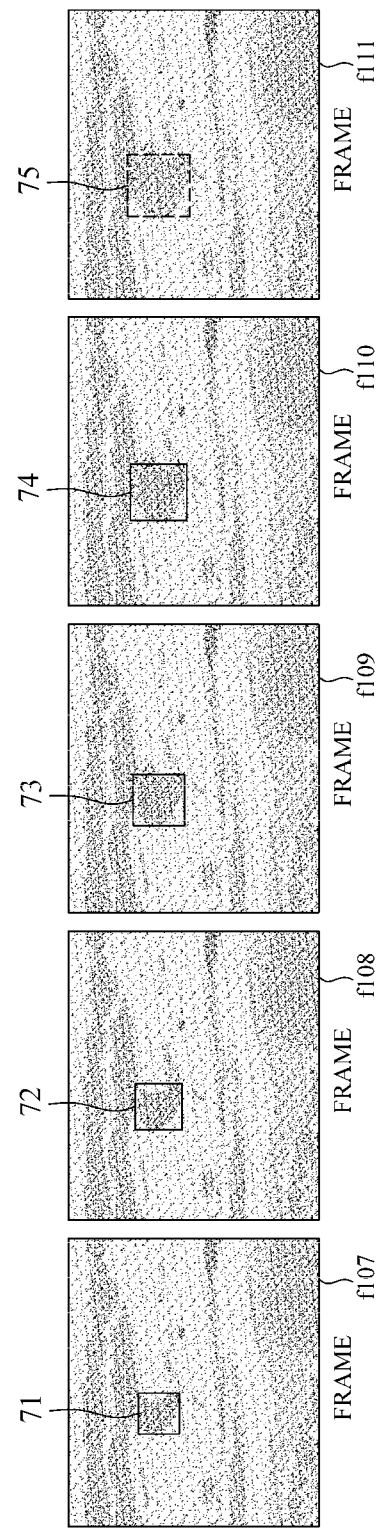
FIGS. 7A and 7B are diagrams illustrating examples of acquiring and outputting of an ROI.
Figure 7B:
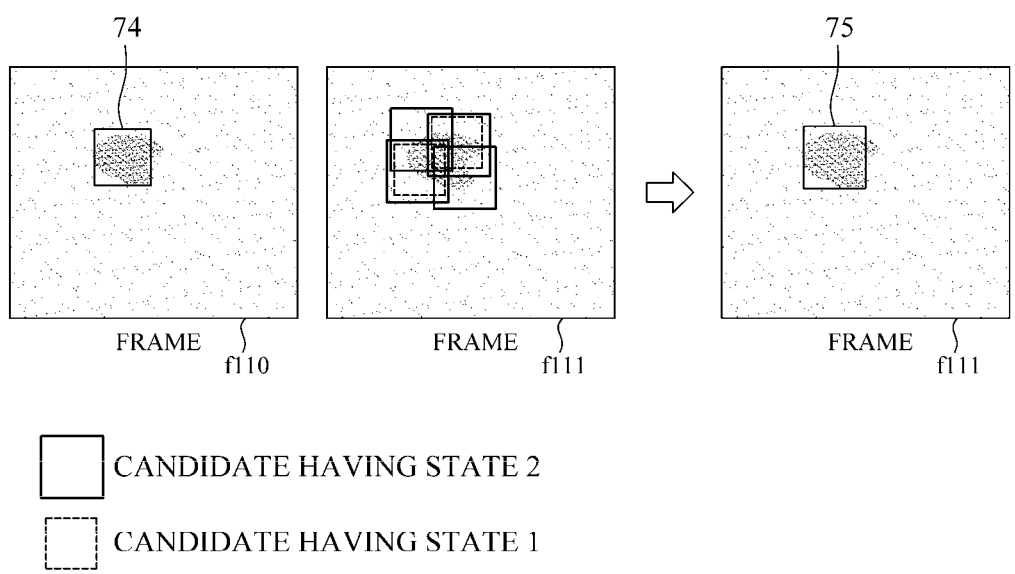

FIGS. 6A and 6B are diagrams explaining acquiring and outputting of an ROI according to an example. FIGS. 7A and 7B are diagrams explaining acquiring and outputting of an ROI according to another example.

FIGS. 6A to 7B illustrate examples of acquiring and outputting an ROI by the Computer Aided Diagnosis (CAD) apparatuses 100 and 300 illustrated in FIGS. 1 and 4. For convenience of explanation, FIGS. 6A to 7B will be described with reference to the CAD apparatus 100 illustrated in FIG. 1, and with reference to an ROI size transition model illustrated in FIG. 5A.

FIG. 6A is a diagram explaining an abnormally big ROI 62 detected from a current frame f105. The size of an ROI detected from a previous frame f104 corresponds to state 1 in an ROI size transition model, and the size of the ROI 62 detected from the current frame f105 corresponds to state 5.

Once the image receiver 110 receives the current frame f105, the ROI acquirer 120 may detect the ROI 62 using an automatic detection algorithm as described above.

Once the ROI 62 is detected from the current frame f105, the ROI acquirer 120 may perform matching by comparing the ROI 61 of the previous frame f104 to the ROI 62 of the current frame f105 in terms of a geo-spatial location and using Jaccard similarity. If the ROI 61 of the previous frame f104 is matched with the ROI 62 of the current frame f105, it is determined to be a normal detection. If they are not matched with each other, the size of the ROI 61 is further matched with an ROI size transition model to determine whether it is an erroneous detection.

If the ROI 61 of the previous frame f104 is not matched with the ROI 62 of the current frame f105, the ROI acquirer 120 matches the size of the ROI 62 with an ROI size transition model, and determines the size of the ROI 62 to be equivalent to that of state 5. Since the size of an ROI may not transition from state 1 to state 5, it may be determined to be an erroneous detection.

The ROI output component 130 determines state 3 to be the biggest possible state to which state 1 of the ROI 61 of the previous frame f104 may transition, and outputs visual information with a size corresponding to the determined size state 3 on a screen to display the ROI 63 of the current image.

FIG. 6B is a diagram explaining three ROIs 65, 66, and 67 detected from the current frame f107, in which it is assumed that the size of the ROI 64 detected from the previous frame f106 is 10 mm, and the size is state 1 in an ROI size transition model.

Once three ROIs 65, 66, and 67 are detected from the current frame f107, the ROI acquirer 120 matches each of the ROIs 65, 66, and 67 with the ROI 64 in the previous frame f106, in which the matching may be performed in terms of a geo-spatial location and using Jaccard similarity.

Once the first ROI 65 of the current frame f107, which is 12 mm in size, is matched with the ROI 64 of the previous frame f106, the ROI acquirer 120 may determine that it is a normal ROI that has been continuously tracked from a previous image, without need for an ROI size transition model.

In this case, the ROI output component 120 may output visual information that includes the detected ROI 65 having a size of 12 mm on a screen to display the ROI 65.

Further, the second and third ROIs 66 and 67 detected from the current frame f107 are new ROIs that have not been detected from the previous frame f106, and thus, are not matched with the previous frame f106. In this case, the ROI acquirer 120 may determine whether the ROIs 66 and 67 are erroneously detected using an ROI size transition model.

In one example, the ROI acquirer 120 may calculate a probability of detecting the ROIs 66 and 67 for the first time, and may determine that the ROIs 66 and 67 are erroneously detected if the calculated detection probability is below a threshold. In this case, the detection probability may be calculated by considering detection scores calculated when ROIs are detected using an automatic detection algorithm, and considering transition probability on an ROI size transition model, in which the detection probability may be calculated by an equation of detection score times transition probability.

For example, if a detection score of the second ROI 66 is 10, and the size on an ROI size transition model is state 2, probability of transition from state 0 where no ROI is detected from a previous image to state 2 is 0.05, with detection probability of 0.5 (0.05×10). Similarly, if a detection score of the third ROI 67 is 25, and the size is state 1, probability of transition from state 0 to state 1 is 0.5, with detection probability of 12.5 (0.5×25). If a predetermined threshold is 10, the second ROI 66 is below the threshold, and thus is determined to be erroneously detected.

As the second ROI 66 is determined to be erroneously detected, the ROI output component 130 does not output visual information for displaying the ROI 66. Further, as the ROI 67 is determined to be detected normally, visual information for displaying the ROI 67 is output. In FIG. 6B, the ROI 66 is shown in a box indicated with "X", which means visual information for the ROI 66 is not output.

FIGS. 7A and 7B are diagrams explaining examples for acquiring and outputting of an ROI according to another example.

FIG. 7A illustrates that with respect to five sequentially input frames f107, f108, f109, f110, and f111, ROIs 71, 72, 73, and 74 which have been detected and tracked from the previous frames f107, f108, f109, and f110 respectively, are not detected from the current frame f111 using an automatic detection algorithm.

If a desired ROI 75 is not detected from the current frame f111 using an automatic detection algorithm, the ROI acquirer 120 may predict an ROI using various types of information calculated by an automatic detection algorithm, e.g., information on candidate regions, detection scores of each of the candidate regions, transition probability for each of the candidate regions, sizes and locations of the ROIs 71, 72, 73, and 74 detected from the previous frames f107, f108, f109, and f110, and the like, so that the ROI 75 may be detected.

For example, if the size of the ROI 74 detected from the previous frame f110 is state 1, the state may transition to any one state of 0, 1, or 2 on an ROI size transition model. In this case, if an ROI, which has been tracked, is not detected from the current frame f111, the ROI acquirer 120 determines whether the size of the ROI normally transitions from 1 to 0.

As shown in the frame f111 illustrated in the middle of FIG. 7B, the ROI acquirer 120 may select neighboring candidate regions, which are positioned within a predetermined threshold from the center of the ROI 74 of the previous frame f110, from among candidate regions of the current frame f111 calculated using an automatic detection algorithm, and using detection scores and sizes of the selected candidate regions, the ROI acquirer 120 may predict the ROI 75.

Referring to FIG. 7B, it may be understood that two candidate regions of state 1 and four candidate regions of state 2 are selected from among candidate regions of states 0, 1, and 2 that may transition from the ROI 74 of the previous frame f110. The ROI acquirer 120 may predict, as the ROI 75, a region with the highest detection probability (e.g., detection score x transition probability) among the selected candidate regions.

Once the ROI 75 is predicted, the ROI output component 130 may output visual information having a size corresponding to the size of the ROI 75 to display the ROI.

Figure 8:
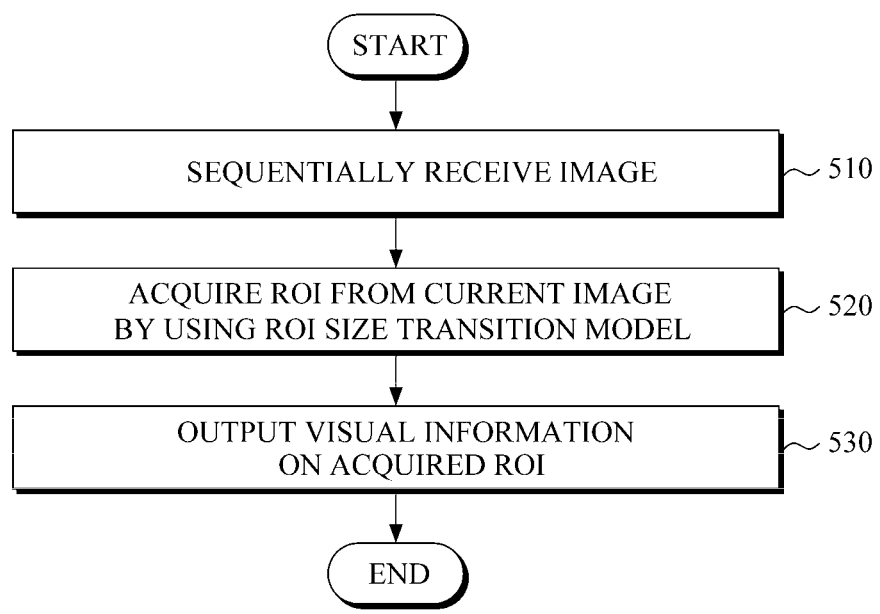
FIG. 8 is a diagram illustrating an example of a Computer-Aided Diagnosis (CAD) method.

FIGS. 8 and 9 are diagrams illustrating examples of a Computer-Aided Diagnosis (CAD) method. FIG. 9 is a diagram illustrating a method of acquiring an ROI. The operations in FIGS. 8-9 may be performed in the sequence and manner as shown, although the order of some operations may be changed or some of the operations omitted without departing from the spirit and scope of the illustrative examples described. Many of the operations shown in FIGS. 8-9 may be performed in parallel or concurrently. The above description of FIGS. 1-7B, is also applicable to FIGS. 8-9, and is incorporated herein by reference. Thus, the above description may not be repeated here.

Examples illustrated in FIGS. 8 and 9 may be performed by the Computer Aided Apparatuses (CAD) 100 and 300 illustrated in FIGS. 1 and 4.

Referring to FIG. 8, in 510, the CAD apparatus sequentially receives images, in which the received images may be ultrasound images acquired through a probe, and may be received in units of frames in real time.

In 520, an ROI is acquired from the received images. The ROI may be acquired using a pre-stored ROI size transition model.

The acquisition of an ROI in 520 may be described in further detail by referring to FIG. 9. In 611, the CAD apparatus detects an ROI from a current image using a pre-stored automatic detection algorithm. Once an ROI desired by a user is detected, in 612, the detected ROI is matched with an ROI detected from a previous image by comparing the ROIs in terms of geo-spatial locations or using Jaccard similarity algorithm. If the ROIs are matched, the detected ROI is determined to be a normal ROI and is output in 619.

If the ROIs are not matched, in 613, the size state of the detected ROI is determined based on a pre-stored ROI size transition model. In 614, it is determined whether the determined size state is appropriate. For example, the size state of an ROI detected from a current image may be matched with the size state of an ROI detected from a previous image of an ROI size transition model. Based on this comparison, it may be determined whether the size state of an ROI detected from a current image could possibly have transitioned from the size state of an ROI detected from the previous image. Based on the comparison, it may be determined whether the determined size state is appropriate.

If it is determined in 614 that the size state of a detected ROI is appropriate, the detected ROI is output in 619.

If it is determined in 614 that the size state of a detected ROI could not have transitioned from the size state of an ROI of a previous image, in 615, it is determined that the ROI is erroneously detected.

In 616, it may be determined whether to output the ROI that has been determined to be erroneously detected. It may be predetermined whether or not to output an erroneously detected ROI. For example, an ROI, which has been tracked from a previous image, may be output in a current image, and if a newly-detected ROI from the current image is erroneously detected, the ROI may not be output.

In 616, if it is determined to output an erroneously detected ROI, the size state appropriate for a detected ROI may be determined in 617 based on an ROI size transition model. An ROI having a size corresponding to the determined size state may be output in 619. For example, if the size state of an ROI detected from a current image may not transition from a size state of an ROI detected from a previous image, the biggest possible size state that may transition from the size state of the ROI of a previous image may be determined to be the size state that may be output.

If an ROI is not detected using an automatic detection algorithm in 612, an ROI that is appropriate for a current image may be predicted in 618 using a pre-stored ROI size transition model. As described above, detection probability may be calculated using detection scores and transition probabilities of candidate regions, which are positioned within a predetermined threshold from the center of the ROI detected from the previous image frame using an automatic detection algorithm. A candidate region having the highest detection probability may be predicted as an ROI of a current image.

Referring back to FIG. 8, in 530, once an ROI is acquired from a current image, visual information is output, which may be output on a screen to inform a user of the ROI. Among ROIs automatically detected in 520, visual information on an ROI, which has been determined to be erroneously detected, may not be output. In another example, if an ROI is a region that has been tracked from a previous image, the size of the detected ROI is matched with an ROI size transition model, so that visual information having a size corresponding to a maximum possible size that may transition from the size of an ROI of a previous image may be output.

The apparatuses, units, modules, devices, and other components illustrated that perform the operations described herein are implemented by hardware components. Examples of hardware components include controllers, sensors, generators, drivers and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array (FPGA), a programmable logic array, a microprocessor, an application-specific integrated circuit (ASIC), or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 8-9 that perform the operations described herein are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A computer program product comprising a non-transitory computer-readable storage medium configured to store a computer readable program comprising instructions, which when executed by a computing device, cause the computing device to:

detect at least one region of interest (ROI) from a current image among sequentially received images;

determine whether at least one ROI, that is erroneously detected, of the detected at least one ROI exists based on an ROI size transition information in the sequentially received images for each of the detected at least one ROI; and
output visual information indicating the at least one ROI except for the erroneously detected at least one ROI based on a result of the determination.

2. The computer program product of claim 1, wherein the sequentially received images are real-time ultrasound images acquired through a probe in units of frames.

3. The computer program product of claim 1, wherein the computing device is further configured to:
determine a size state of the detected at least one ROI by matching a size of the detected at least one ROI with the ROI size transition information; and
determine that the detected at least one ROI is erroneously detected, in response to determining that a size state of a previous image on the ROI size transition information is not capable of being transformed to the determined size state of the current image.

4. The computer program product of claim 3, wherein the computing device is further configured to not output visual information on the at least one ROI that is erroneously detected.

5. The computer program product of claim 3, wherein the computing device is further configured to:
in response to the at least one ROI being erroneously detected, determine the biggest size state that is possible to transition from the size state of the previous image using the ROI size transition information, and
output visual information to a size corresponding to the biggest size state.

6. The computer program product of claim 1, wherein the computing device is further configured to predict an ROI in the current image using the ROI size transition information, in response to the ROI not being detected from the current image.

7. The computer program product of claim 6, wherein the computing device is further configured to:
determine a size state transitionable from the size state of the ROI on an image before the current image using the ROI size transition information, and
predict the ROI in the current image using the determined size state.

8. The computer program product of claim 1, wherein the ROI size transition information is created using a Markov model learning based on a change in sizes of ROIs in a sequence of images for each interested item, and the ROI size transition information comprises size states, a transition possibility between the size states, transition direction, and transition probability information.

9. The computer program product of claim 1, wherein, in order to indicate a location and size of the outputted at least one ROI in the current image, the visual information includes:
first information comprising at least one of square, round, oval, or cross shapes; and
second information comprising at least one of color, types of lines, or thickness of lines of the first information.

10. The computer program product of claim 1, wherein the sequentially received images are configured to a three-dimensional image.

11. A computer aided diagnosis (CAD) method, comprising:
sequentially receiving images;
detecting at least one region of interest (ROI), by a processor, from a current image among the sequentially received images;
determining whether at least one ROI, that is erroneously detected, of the detected at least one ROI exists based on an ROI size transition information; and
outputting visual information that indicates the at least one ROI except for the erroneously detected at least one ROI based on a result of the determination.

12. The CAD method of claim 11, wherein the determining comprises:
determining a size state of the detected at least one ROI by matching a size of the detected at least one ROI with the ROI size transition information; and
determining that the detected at least one ROI is erroneously detected, in response to determining that a size state of a previous image on the ROI size transition information is not capable of being transformed to the determined size state of the current image.

13. The CAD method of claim 12, further comprising:
not outputting visual information on the at least one ROI that is erroneously detected.

14. The CAD method of claim 12, wherein the outputting comprises:
determining the biggest size state that is possible to transition from the size state of the previous image using the ROI size transition information; and
outputting visual information to a size corresponding to the biggest size state.

15. The CAD method of claim 11, further comprising:
predicting an ROI in the current image using the ROI size transition information in response to the ROI not being detected from the current image.

16. The CAD method of claim 15, wherein the predicting of the ROI comprises:
determining a size state transitionable from the size state of the ROI on an image before the current image using the ROI size transition information; and
predicting the ROI in the current image using the determined size state.

17. The CAD method of claim 11, wherein the ROI size transition information is created using a Markov model learning based on a change in sizes of ROIs in a sequence of images for each interested item, and the ROI size transition information comprises size states, a transition possibility between the size states, transition direction and transition probability information.

18. The CAD method of claim 11, wherein the sequentially receiving of the images comprises:
receiving real-time ultrasound images through an image receiver in units of frames.

19. The CAD method of claim 11, wherein the sequentially received images are configured to a three-dimensional image.

20. A computer aided diagnosis (CAD) apparatus, comprising:
a memory configured to store instructions; and
at least one processor, that upon executing the stored instructions, configured to:
detect at least one region of interest (ROI) from a current image among sequentially received images,
determine whether at least one ROI, that is erroneously detected, of the detected at least one ROI exists based on an ROI size transition information, and
output visual information indicating the at least one ROI except for the erroneously detected at least one ROI based on a result of the determination.

* * * * *